United States Patent [19]

Erickson

[11] Patent Number: 4,723,033

[45] Date of Patent: Feb. 2, 1988

[54] MANUFACTURE OF OPTICALLY ACTIVE α-ARYLALKANOIC ACIDS AND PRECURSORS THEREOF

[75] Inventor: Gary W. Erickson, Boulder, Colo.

[73] Assignee: Syntex Pharmaceuticals International Ltd., Bermuda

[21] Appl. No.: 837,442

[22] Filed: Mar. 7, 1986

Related U.S. Application Data

[63] Continuation-in-part of Ser. No. 444,109, Nov. 24, 1982, abandoned.

[51] Int. Cl.$^4$ .................... C07C 67/30; C07C 51/00; C07C 102/00; C07C 120/00; C07D 263/08
[52] U.S. Cl. .................................. 560/56; 548/237; 548/240; 558/354; 562/401; 562/466; 564/172
[58] Field of Search ............... 562/401, 466; 560/56; 564/172; 548/237, 240; 558/354

[56] References Cited

U.S. PATENT DOCUMENTS

| | | | |
|---|---|---|---|
| 3,651,106 | 3/1972 | Harrison | 562/466 |
| 3,652,683 | 3/1972 | Harrison | 562/466 |
| 3,658,858 | 4/1972 | Harrison | 562/466 |
| 3,658,863 | 4/1972 | Harrison | 562/466 |
| 3,663,584 | 5/1972 | Alvarez | 562/466 |
| 3,694,476 | 9/1972 | Alvarez | 562/466 |
| 3,959,364 | 5/1976 | Armitage et al. | 562/466 |
| 3,994,968 | 11/1976 | Alvarez | 562/466 |
| 4,142,054 | 2/1979 | Amin et al. | 562/466 |
| 4,239,914 | 12/1980 | Campolmi et al. | 562/466 |
| 4,423,244 | 12/1983 | Cannata et al. | 562/466 |

FOREIGN PATENT DOCUMENTS

0033233  8/1981  European Pat. Off. .

OTHER PUBLICATIONS

Bull. Chem. Soc. Japan., v. 49, No. 7, pp. 1958–1969 (1976), K. Tamao et al.
Tet. Lett., v. 21, pp. 79–82 (1980), T. Hayashi et al.
Tet. Lett., No. 51, pp. 4697–4700 (1976), T. Baer et al.
Helvetica Chimica Acta, v. 56, fasc. 1, No. 36 (pp. 460–463), 1973, G. Consiglio et al.

*Primary Examiner*—Werren B. Lone
*Assistant Examiner*—Vera C. Clarke
*Attorney, Agent, or Firm*—Derek P. Freyberg; John A. Dhuey

[57] ABSTRACT

This invention concerns a new process of preparing optically active α-arylalkanoic acids and their precursors. These α-arylalkanoic acids, esters, amides, nitriles, oxazolines and metal salts are stereoselectively prepared by forming the metal or metal halide of the corresponding acid, ester, amide, oxazoline, nitrile, or metal salt and treating the compound so prepared with an aryl halide in the presence of a chiral (optically active) transition metal catalyst of the formula (LL*)QZT wherein Q is a transition metal selected from palladium and nickel; Z and T are independently halogen; and LL* is a chiral tertiary diphosphine compound capable of acting as a bidentate ligand with Q to form a 5-membered ring, optionally in the presence of a dipolar aprotic solvent or mixtures thereof, for a time sufficient to form the corresponding optically active α-arylalkanoic acid, ester, amide, nitrile, oxazoline or metal salt, and optionally concomitantly or sequentially hydrolyzing any ester, amide, nitrile, oxazoline or metal salt formed to the corresponding optically active α-arylalkanoic acid. The process optionally further includes removal of halogen atom from the aromatic portion of the α-arylalkanoic acid. The process optionally includes subsequent formation of the pharmaceutically acceptable salts and esters of the optionally active α-arylalkanoic acid. This is a simple process for the preparation of the described optically active α-arylalkanoic acids. These compounds are useful as pharmaceutical (e.g., anti-inflammatory) agents.

10 Claims, No Drawings

MANUFACTURE OF OPTICALLY ACTIVE α-ARYLALKANOIC ACIDS AND PRECURSORS THEREOF

CROSS REFERENCE TO RELATED APPLICATION

This application is a continuation-in-part of my copending, commonly-assigned application Ser. No. 444,109, filed Nov. 24, 1982, entitled "Manufacture of Optically Active α-arylalkanoic Acids and Precursors Thereof", the entire disclosure of which is incorporated herein by reference, now abandoned.

BACKGROUND OF THE INVENTION

1. Field of the Invention

The present invention relates to processes for preparing optically active α-arylalkanoic acids and the novel intermediates utilized therein. In particular, it relates to a stereoselective process for the preparation of optically active α-arylalkanoic acids by the oxidative coupling of the α-substituted metal or metal salt of an acid or derivative of an acid with an aryl halide in the presence of a chiral (optically active) transition metal catalyst, optionally in the presence of a dipolar, aprotic solvent. Optionally, concomitant or sequential hydrolysis of the derivative, such as the ester, amide, oxazoline, nitrile or carboxylic metal salt formed produces the corresponding optically active α-arylalkanoic acid. The process optionally includes the subsequent removal of halogen from the aromatic portion of the α-arylalkanoic acid. The process further includes subsequent formation of the pharmaceutically acceptable salts and esters of the optically active α-arylalkanoic acids. The products are pharmaceutical agents which have anti-inflammatory, analgesic and anti-pyretic activities.

2. State of the Art

Numerous α-arylalkanoic acids (i.e. 2-arylalkanoic acids) have been described and developed and found to be useful as pharmaceutical agents exhibiting anti-inflammatory, analgesic and anti-pyretic activity. For example, U.S. Pat. No. 3,385,386, describes certain 2-phenylpropionic acids useful for their anti-inflammatory activity. Particularly noteworthy of the compounds described therein is 2-(4-isobutylphenyl)propionic acid, known generically as ibuprofen. U.S. Pat. No. 3,600,437 describes 2-(3-phenoxyphenyl)- and 2-(3-phenylthiophenyl)alkanoic acids among other related compounds. Particularly noteworthy therein is the compound 2-(3-phenoxyphenyl)propionic acid, which is known generically as fenoprofen. U.S. Pat. No. 3,624,142 describes (fluoro-substituted biphenyl)alkanoic acids, among which is 2-(4'-fluoro-4-biphenyl)-propionic acid. U.S. Pat. No. 3,755,427 describes additional fluoro-substituted biphenylpropionic acids, among which is 2-(2-fluoro-4-biphenyl)propionic acid, known as flurbiprofen. U.S. Pat. No. 3,904,682 describes the compound 2-(6-methoxy-2-naphthyl)propionic acid, which is known generically as naproxen and is a potent anti-inflammatory compound. Related compounds are described in Belgian Pat. No. 747,812. U.S. Pat. No. 3,912,748 describes 5- and 6-benzoxyazoyl-alkanoic acids possessing anti-inflammatory, anti-pyretic and analgesic activity. Notable among those compounds is 2-(4-chlorophenyl-5-benzoxazoyl)-propionic acid, known generically as benoxaprofen. Thus, it can be seen that a tremendous variety of useful α-arylalkanoic acids are known.

Other known, useful α-arylalkanoic acids are exemplified by 6-chloro-α-methyl-9H-carbazole-2-acetic acid (carprofen), α-methyl-9H-fluorene-2-acetic acid (cicloprofen), 3-chloro-α-methyl-4-(2-thienylcarbonyl)-benzene acetic acid (cliprofen), α-methyl-3-phenyl-7-benzofuranacetic acid (furaprofen), 4-(1,3-dihydro-1-oxo-2H-isoindol-2-yl)benzene acetic acid (indoprofen), 3-benzoyl-α-methylbenzene acetic acid (ketoprofen), 3-chloro-4-(2,5-dihydro-1H-pyrrol-1-yl)benzeneacetic acid (pirprofen), α-methyl-4-(2-thienylcarbonyl)benzeneacetic acid (suprofen) and compounds related thereto.

Numerous processes for the manufacture of such α-arylalkanoic acids have also been described. Such processes have been described in the aforementioned patents, and in other patents and in the non-patent literature as well. For example, U.S. Pat. No. 4,135,051 describes a process for preparing the ester precursors of many arylalkanoic acids utilizing trivalent thallium salts as reactants. Such a process suffers from the disadvantage that the thallium salts employed are toxic chemicals which must be removed from the final product. U.S. Pat. No. 3,975,431 describes the preparation of α-arylalkanoic acids from glycidonitriles through enol acylates. U.S. Pat. Nos. 3,658,863; 3,663,584; 3,658,858; 3,694,476; and 3,959,364 describe various coupling methods for preparing arylalkanoic acids. More recently, U.K. Patent publication No. 2,042,543, published Sept. 24, 1980, (corresponding to application Ser. No. 8005752, filed Feb. 20, 1980) describes a process for preparing the ester precursor of arylalkanoic acids from α-haloalkyl aryl ketones using a metal catalyst for catalytically inducing rearrangement in an acidic, alcoholic medium, the catalyst being silver (I) salts of organic and/or inorganic anions. The high costs associated with utilizing certain metal catalysts, particularly silver catalysts, in a large scale process is an inherent disadvantage to such a process.

U.S. Pat. No. 3,652,683 describes the preparation of 2-(6-methoxy-2-naphthyl)propionic acid by reacting a 2-(1-haloethyl)-6-methoxynaphthylene with nickel carbonyl in a lower tertiary alkanol solvent in the presence of an alkyl metal tertiary alkoxide until the ester is formed, and subsequently hydrolyzing the ester group thereof.

U.S. Pat. No. 3,651,106 describes a coupling of ethyl naphthalene derivatives, substituted in the α-position with a metal with: (a) carbon dioxide to produce the corresponding carboxylic acid; (b) ethyl orthocarbonate to produce the corresponding ester; (c) ethyl chloroformate; or (d) paraformaldehyde to produce the corresponding aldehyde which is reacted further to produce the corresponding 2-(6-methoxy-2-naphthyl)propionic acid.

Additional related patents include U.S. Pat. Nos. 3,076,016; 3,907,850; 4,017,526; 4,055,582; 4,120,882; 4,133,963; 4,142,054; 4,144,259; 4,293,502; 4,239,914; and 4,306,086, all of which are incorporated herein by reference.

The production of α-arylkanoic acids by the arylation of $BrZn-CH_2CO_2CH_2CH_3$ using unsubstituted aromatic halides has been reported by J. F. Fauvarque and A. Jutand in the *Journal of Organometallic Chemistry*, Vol. 177, pp. 273–281 (1979).

The preparation of phenyl alkylcarboxylic acid esters by treatment of the corresponding α-lithium substituted carboxylic ester with unsubstituted phenyl halides in the presence of an inorganic nickel halide catalyst and a dipolar aprotic solvent, was reported by A. A. Millard and M. W. Rathke in *J. Amer. Chem. Soc., Vol.* 99, pp. 4833–4837 (1977). Other reactions of Grignard reagents with alkyl halides in the presence of a catalyst have been reported by T. Hayashi, et al., *J. Amer. Chem. Soc.,* Vol. 104, pp. 180–186 (1982); T. Hayashi, et al., *J. Amer. Chem. Soc.,* Vol. 98, pp. 371–819, (1976); K. Tamao, et al., *Bulletin of the Chemical Society of Japan,* Vol. 49, No. 7, pp. 1958–1969 (1976); and T. Hayashi, et al., *Tet. Lett.,* Vol. 21, pp. 79–82 (1980).

B. J. Wakefield, in the *Chemistry of Organolithium Compounds,* published by Pergamon Press of New York in 1974, and references cited therein discusses the reverse metal-halogen exchange for organolithium compounds. This reaction appears to require highly activated unsaturated or alkyl-multiple halogen compounds to occur with organolithium compounds, and because optically active acids are obtained from the process, the exchange is not expected in the process of this invention. Similarly, T. Baer and R. Carney in *Tetrahedron Letters,* No. 51, pp. 4697–4700 published in 1976 discuss the copper catalyzed reaction of Grignard reagents with chloromagnesium salts of lower case ω-bromoacids.

Notwithstanding the usefulness of the aforesaid processes in many respects, there still remains a need for a simple process for producing optically active α-arylalkanoic acids of the types described. A number of the α-arylalkanoic acids exist as a mixture of optical isomers. It is often advantageous to have a stereoselective process for producing the desired optically active isomer of the α-arylalkanoic acid which displays all or a major portion of the pharmaceutical activity. For example, the isomer d 2-(6-methoxy-2-naphthyl)propionic acid is more pharmaceutically active than the 1-isomer. Therefore, it is desirable to have a stereoselective process for producing the d-isomer directly. Such a process obviates the necessity of subsequently resolving the d- and l-isomers using optically active bases, such as cinchonidine, brucine, and the like. The elimination of the resolution steps results in a substantial savings, both in material cost and manufacturing labor and equipment. The savings can be particularly significant with regard to compounds which are approved for pharmaceutical use as a substantially pure, optically active isomer, such as d 2-(6-methoxy-2-naphthyl)propionic acid (naproxen) or a precursor which may be easily converted to this acid.

SUMMARY OF THE INVENTION

The present invention describes a process for preparing an optically active compound of the formula:

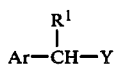  (I)

wherein:
Ar is an aryl moiety;
$R^1$ is lower alkyl having 1–8 carbon atoms inclusive or cycloalkyl having 3–8 carbon atoms inclusive; and
Y is a carboxyl group, a metal salt of a carboxyl group, an alkoxycarbonyl group, a substituted aminocarbonyl group, a nitrile or an oxazolinyl group;

which comprises:
contacting a compound of the formula:

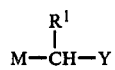  (II)

wherein:
$R^1$ and Y are as defined above, and
M is lithium, tin, tin halide, zinc, or zinc bromide, with an aryl halide of the formula:

  (III)

wherein:
Ar is as defined above and X is halogen, in the presence of a chiral (optically active) transition metal catalyst of the formula (LL*)QZT wherein Q is a transition metal selected from palladium and nickel; Z and T are independently halogen; and LL* is a chiral tertiary diphosphine compound capable of acting as a bidentate ligand with Q to form a 5-membered ring and optionally in the presence of a dipolar, aprotic solvent to form the compound of formula I, and the pharmaceutically acceptable salts thereof.

In another aspect of this invention, the process further includes the dehalogenation of certain halogen substituted naphthalene derivatives, which are precursors to naproxen, such as 2-(5-bromo-6-methoxy-2-naphthyl)propionic acid to naproxen.

In the process of the present invention a catalytic coupling of an acid, ester, amide, nitrile, oxazoline or metal salt of an alkyl carboxylic acid with an aryl halide is effected by direct metallation or by activation of the carbon in the α-position to the carbonyl with a metal or metal halide to form the corresponding metal, i.e. —CH(M)-acid, —CH(M)-ester, —CH(M)-amide, —CH(M)-nitrile, —CH(M)-oxazoline, or carboxylic metal salt, —CH(M)C(O)OM, where M is the metal ion. The aryl halide, such as 6-methoxy-2-bromonaphthalene, is chosen to be sufficiently labile so as to react with the metal derivative in the presence of the chiral (optically active) transition metal catalyst, optionally in the presence of a dipolar, aprotic solvent medium. The reaction mixture is maintained for sufficient time to form the corresponding optically active α-arylalkanoic acid, ester, amide, nitrile, oxazoline or metal salt. Optionally, concomitantly or sequentially hydrolyzing any of the above derivatives affords the corresponding α-arylalkanoic acid.

In another aspect, this invention is directed to a process for the preparation of a stereoisomer, particularly a single stereoisomer, of α-arylalkanoic acids and their pharmaceutically acceptable salts.

In another aspect, this invention is directed to a process for the preparation of a material consisting essentially of a single stereoisomer of α-arylalkanoic acids by the treatment of a α-metal derivative of an acid, ester amide, nitrile, oxazoline, or carboxyl metal salt with an aryl halide in the presence of a chiral (optically active) transition metal catalyst, optionally in the presence of a dipolar, aprotic solvent, with optional hydrolysis of any ester, amide, nitrile, oxazoline or metal salt formed to the desired acid.

Each of the processes described above includes:
(a) concomitantly or sequentially hydrolyzing any ester, amide, nitrile, oxazoline or metal salt formed to the corresponding α-arylalkanoic acid, optionally followed by;

(b) hydrolyzing a salt or ester corresponding to the free acid of formula I into said free acid by treating with acid; or (c) esterifying the free acid of formula I by treating with an alkanol; or (d) converting the free acid of formula I into a pharmaceutically acceptable salt by treating with a pharmaceutically acceptable base without loss of optical activity.

In another aspect, this invention is directed to certain novel intermediates useful in the preparation of optically active α-arylalkanoic acids.

DETAILED DESCRIPTION OF THE INVENTION

Definitions

As used herein:

"Alkoxycarbonyl group" refers to an ester group, i.e. $-COOR^3$ wherein $R^3$ is independently selected from the same alkyl groups as $R^1$ above.

"Alkyl" refers to alkyl groups having 1 to 8 carbon atoms inclusive and is exemplified by methyl, ethyl, n-propyl, i-propyl, n-butyl, i-butyl, s-butyl, t-butyl, n-hexyl and n-octyl and the like.

"Alkanol" refers to an organic alcohol incorporating one of the "alkyl" groups described above.

"Alkoxy" refers to alkoxide groups (i.e., $R^3O-$) having 1–8 carbon atoms and are exemplified by methoxy, ethoxy, n-propoxy, i-propoxy, n-butoxy, i-butoxy, t-butoxy, n-hexoxy, n-octoxy and the like.

"Aryl" refers to unsubstituted or substituted phenyl, phenoxyphenyl, naphthyl or biphenyl groups such as those represented by 3-phenoxyphenyl, 2-fluoro-1-biphenyl, 4-isobutylphenyl, 1-fluoro-4-biphenyl, 5-bromo-6-methoxy-2-naphthyl, 5-chloro-6-methoxy-2-naphthyl, 6-hydroxy-2-naphthyl and 6-methoxy-2-naphthyl. The optional substituents on the phenyl, phenoxyphenyl, biphenyl and naphthyl groups are exemplified by lower alkyl having 1 to 4 carbon atoms inclusive, such as methyl, ethyl, n-propyl, i-propyl, n-butyl, i-butyl and t-butyl; lower alkoxy groups having 1 to 4 carbon atoms inclusive such as methoxy, ethoxy, n-propoxy, iso-propoxy, t-butoxy and the like; hydroxyl; hydroxyl salts; and halogen, such as chloro, bromo, or fluoro.

"Chiral" refers to a chemical structure having an asymmetric center.

"Cycloalkyl" refers to cyclic hydrocarbon groups having from 3–8 carbon atoms such as cyclopropyl, cyclobutyl, cyclopentyl, methyl cyclopentyl, cyclopentylmethyl, cyclohexyl, cyclooctyl and the like.

"Dipolar aprotic solvent" includes such solvents as, but is not limited to, benzene, toluene, dibutyl ether, dimethoxyethane, diethyl ether, hexamethylphosphoramide, hexane, hexene, pentane, petroleum ether, tetrahydrofuran, N-methylpyrrolidone, and the like. Mixtures of these solvents and inert diluents, e.g., hydrocarbon solvents, are also useful in this invention.

"Enantiomer" or "enantiomorph" refers to a molecule which is non-superimposable on its respective mirror image. A necessary and sufficient condition for a molecule to show optical activity (i.e. an enantiomer) is that such a molecule not be superimposable with its mirror image. This phenomena usually occurs in organic chemistry with a carbon atom is attached to four different atoms or chemical groups. "Enantiomer" and "optical isomer" are often used interchangeably in this context.

"Enantiomeric excess" or "e.e." refers to a definition; i.e. as the percentage of the predominant enantiomer minus that of the other. Thus, a mixture of 95%(+) isomer and 5%(−) isomer would have a 90% e.e.

"Grignard reagent" refers to an alkyl or aryl magnesium halide such as ethyl magnesium chloride, methyl magnesium bromide, phenyl magnesium bromide, p-methylphenyl magnesium iodide, and the like. Any combination of alkyl or aryl or halogen group is useful.

"Halogen" or "X" is exemplified by bromine, iodine, chlorine and fluorine. Usually, the order of preference of ArX in this invention is the selection of an aryl iodide over an aryl bromide over an aryl chloride. The yields of product (I) usually decrease in order of aryl iodide to aryl bromide to aryl chloride in this reaction.

"Metal" or "M" refers to lithium, tin, tin halide (chloride, bromide or iodide), zinc or zinc bromide. The metal may be introduced directly into the acid, ester, amide, oxazoline or nitrile by the use of an alkyl or aryl metal, or by treatment with the metal or an organic metal base of sufficient strength to remove a proton under suitable conditions.

"Metallation" or "metallated" refers to the formation of a metal-carbon bond (M—C—), e.g. Li—C—, or, in some cases, of a halogen-metal-carbon bond (X—M—C—), e.g., Br—Zn—C— or Cl—Sn—C—.

"Metal salt of a carboxyl group" refers to a —COOM group, wherein M may be lithium, tin, tin halide (chloride, bromide, iodide), zinc or zinc bromide.

"Nitrile" refers to an organic compound containing a cyano (—C≡N) group.

"Optical yield" or "optical purity" is defined analogously to enantiomeric excess. However, strictly speaking it refers to the measured rotation of the mixture which may or may not reflect the true proportions of the enantiomers. In this application, the two terms are more or less used interchangeably.

"Optically active" refers to an operational term meaning that the system or compound will rotate the plane of polarized light.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that the conversion may or may not be carried out in order for the process described to fall within this invention, and that this invention includes those processes wherein the free base is converted to the acid addition salt and those processes in which it is not.

"Oxazolinyl group" refers to a cyclic protecting group of the formula

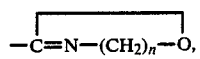

wherein n is an integer from 1–5.

"Pharmaceutically acceptable non-toxic esters" of formula I are those compounds wherein the —OH portion of the —COOH group of formula I is replaced by alkoxy of 1-12 carbon atoms. These are discussed in more detail below and in Example 35 by reacting the appropriate alcohol with the acid of formula I.

"Pharmaceutically acceptable non-toxic salt" refers to derivatives of the compounds of formula I wherein the —H of the —COOH group is replaced by a positive ion such as sodium, for example, or is combined with a suitable amine. These are discussed hereafter in more detail and also in Example 33 by reacting the acid of formula I with a suitable base.

"Protection" or "protecting group" refers to protection of a carboxyl group by conversion to a metal salt, an ester, amide, oxazoline, or nitrile with subsequent regeneration of the carboxylic acid at a later time.

"Substituted aminocarbonyl group" refers to a disubstituted amide of the formula —C(O)NR$^4$R$^5$, wherein R$^4$ and R$^5$ are independently selected from the same alkyl groups as R$^1$ as described above.

"Transition metal catalyst" (e.g., useful in Step B) is a catalyst of the formula (LL*)QZT wherein Q is a transition metal selected from palladium and nickel; Z and T are independently halogen; and LL* is a chiral tertiary diphosphine compound capable of acting as a bidentate ligand with Q to form a 5-membered ring, i.e. a chiral ethylenically-bridged diphosphine ligand. Suitable such compounds include substituted 1,2-diphosphinoethanes [typically, substituted 1,2-bis(diphenylphosphino)ethanes, e.g., 1- or 1,2-(alkyl or aryl)-substituted-1,2-bis(diphenylphosphino)ethanes], substituted 1,2-diphosphinocyclohexanes [typically, substituted 1,2-bis(diphenylphosphino)cyclohexanes], and the like. Such optically active catalysts include CHIRAPHOS, PHENPHOS, PROPHOS as the nickel or palladium halides and others described herein.

General Aspects of the Process

A direct method of preparing the optically active arylalkanoic acid of this invention is to convert the corresponding aliphatic acid to obtain the mono- or di-metal substituted derivative, and further react said derivative with aryl halide in the presence of a chiral (optically active) transition metal catalyst, optionally in the presence of a dipolar aprotic solvent, to produce the compound of formula I and, if necessary, hydrolyze I to the corresponding Ar—CH(R$^1$)—COOH.

Alternatively, the carboxyl group of the alkanoic acid may be converted to a derivative, i.e., by using a protecting group, such as an ester, amide, nitrile or oxazoline; which may be halogenated and metallated, to produce a metallated compound which is further reacted with an aryl halide as is described above.

Also, the carboxyl group of the alkanoic acid, under certain circumstances, may be metallated directly and the carboxyl group thus protected further reacted to produce an α-metallated, carboxyl protected compound which is then further reacted with an aryl halide as is described above.

In addition, the carboxyl group of the alkanoic acid may be protected as the ester, amide, nitrile or oxazoline and metallated to produce a metallated and protected derivative which is further reacted with an aryl halide as is described above. The conversion of the carboxylic acid, R$^1$—CH$_2$—COOH, to the dilithium dianion of the carboxylic acid is a presently preferred process, and is described with regard to propionic acid where R$^1$ is methyl in Example 3 below. In the subsequent reaction aryl halide (ArX) and a chiral (optically active) catalyst are used to produce the compound of formula I. Again, in the case of the dilithium compound, the reaction proceeds in high yield to produce optically active Ar—CH(R$^1$)-COOM, and a normal hydrolysis will produce the desired opticallyactive arylalkanoic acid, Ar—CH(R$^1$)—COOH. Lithium may be incorporated by use of an alkyl or aryl lithium, such as n-butyllithium or phenyllithium, in an inert solvent such as tetrahydrofuran at reduced temperatures. Typically, N,N-diisopropylamine, n-butyllithium and propionic acid are combined at 0° C. and allowed to warm to ambient temperature over a few hours. A presently preferred metal is lithium.

REACTION SEQUENCE OF THE PROCESS

An illustrative reaction sequence is shown below:

REACTION SEQUENCE 1

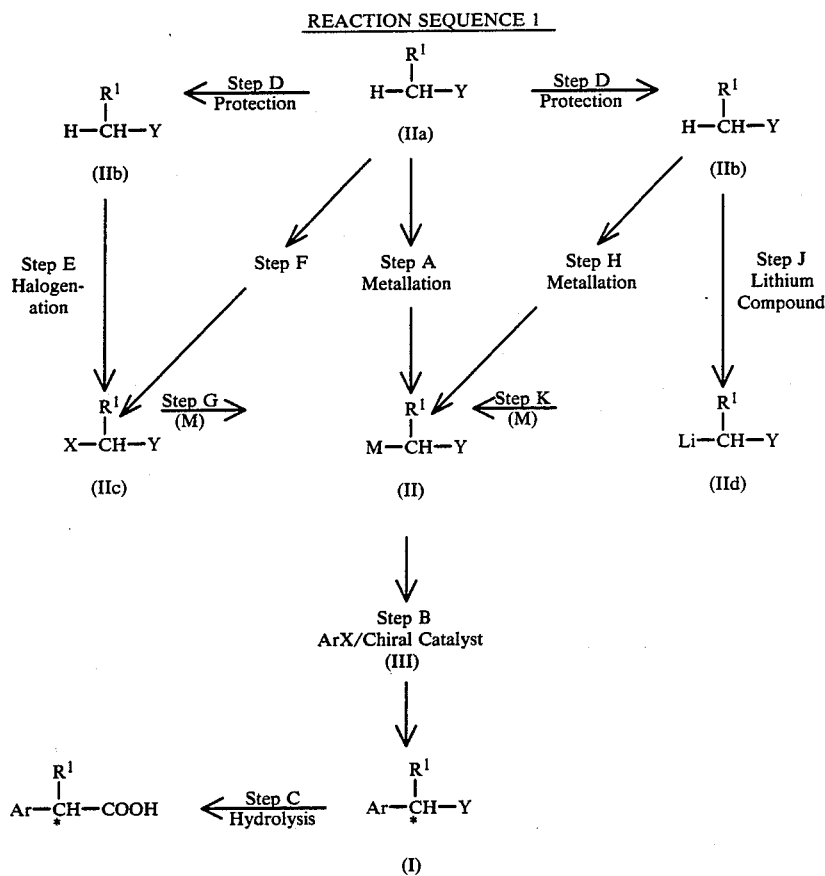

*denotes the asymmetric carbon atom.

The Process

Steps A, B, and C

In one aspect compounds of formula I are prepared wherein the carboxyl group is used directly (steps A, B and C). A starting material of formula IIa may be purchased from commercial sources or by preparation of the corresponding substituted carboxylic acid, i.e., $R^1$—$CH_2$—COOH (formula IIa) usiing conventionally available methods. Compound (IIa) is treated with a strong base in Step A, such as n-butyllithium or lithium diisopropylamide, which produces the metallated compound (II). In other examples the metal "M" introduced may also be lithium, tin, or tin halide, zinc or zinc bromide. In the case of lithium, the dilithium dianion, $Li^+{}^-CH(R^1)$—$COO^-Li^+$, is produced as compound II.

Some of these aryl halides used in this invention may be purchased or may be produced according to methods which are known to those skilled in the art.

The chiral (optically active) transition metal catalysts are known in the art, for instance, the preparation of [(R)-1,2bis(diphenylphosphonio)-1-phenylethane]nickel(II) chloride is performed according to B. Booth and J. Chatt, *J. Chem. Soc.*, 3238 (1965), which is incorporated herein by reference. Chiral (optically active) transition metal catalysts derived from other phosphines are prepared in a similar manner as described by R. E. Merrill in "Asymmetric Synthesis using Chiral Phosphine Ligands" by Reactor Design Corporation, 100 Hoffman Place, Hillside, N.J. 07205, Copyright 1980, which is incorporated herein by reference.

In this reaction (Step B) the chiral (optically active) transition metal catalysts may be treated with a Grignard reagent, such as ethyl magnesium chloride, EtMgCl, or other reducing agent with excess alkyl or aryl metal, such as n-butyllithium, which reduces the oxidations state of the metal, for instance, from $M^{+1}$ or $M^{+2}$ to $M^o$.

The chiral transition metal catalysts include many optically active cyclic organic nickel or palladium phosphorus halide derivatives. Cyclic derivatives of the type of structure shown below in Table 1 are exemplary:

TABLE 1

Chiral (Optically Active) Transition Metal Catalysts

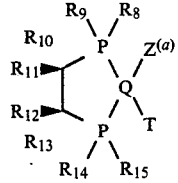

| No. | $R_8$ | $R_9$ | $R_{10}$ | $R_{11}$ | $R_{12}$ | $R_{13}$ | $R_{14}$ | $R_{15}$ |
|---|---|---|---|---|---|---|---|---|
| $C^{1(b)}$ | φ | φ | $CH_3$ | H | $CH_3$ | H | φ | φ |
| $C^{2(c)}$ | φ | φ | H | φ | H | H | φ | φ |

TABLE 1-continued

Chiral (Optically Active) Transition Metal Catalysts

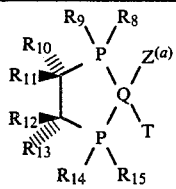

| No. | R$_8$ | R$_9$ | R$_{10}$ | R$_{11}$ | R$_{12}$ | R$_{13}$ | R$_{14}$ | R$_{15}$ |
|---|---|---|---|---|---|---|---|---|
| C$^{3(d)}$ | φ | φ | H | CH$_3$ | H | H | φ | φ |

(a) Q is a transition metal selected from palladium or nickel, and T and Z are independently halogen, usually chlorine.
(b) C$^1$ is CHIRAPHOS nickel(II) chloride, when Q is nickel and T and Z are chloro; i.e. [(R)—1,2-bis(diphenylphosphino)-1,2-dimethyl-ethane]nickel(II) chloride.
(c) C$^2$ is PHENPHOS nickel(II) chloride, when Q is nickel and T and Z are chloro; i.e. [(R)—1,2-bis(diphenylphosphino)-1-phenylethane]nickel(II) chloride.
(d) C$^3$ is PROPHOS nickel(II) chloride, when Q is nickel and T and Z are chloro; i.e. [(R)—1,2-bis(diphenylphosphino)1-1-methylethane]nickel(II) chloride.

In any particular embodiment of this invention the coupling of aryl halide to the compound of formula II can be optionally conducted in the presence of a dipolar, aprotic solvent, which has been defined above.

In Step C, Compound I is hydrolyzed under acidic or basic conditions, which are known to those skilled in the art, to produce the free optically active acid, Ar—CH(R$^1$)—COOH.

Steps D, H, B, and C

In another aspect of the process of this invention, compounds of formula I are prepared by protection in some way of the carboxyl groups (Step D) by formation of an intermediate, R$^1$—CH$_2$—Y (formula II(b)) wherein R$^1$ and Y are as described above, which is converted (Step H) to a suitable α-metal substituted derivative. After coupling with ArX (Step B), Compound I is ultimately reconverted into a carboxylic acid (Step C).

These protected compounds (i.e. IIb) are known in the art and include a metal salt of a carboxyl group, alkoxycarbonyl (esters), substituted aminocarbonyl (amides), oxazolinyl (oxazolines), and nitriles, and may be produced by methods known in the art.

In other words, the protection of the carboxyl group (Step D), i.e., by the conversion of R$^1$—CH$_2$COOH to R$^1$—CH$_2$—Y (IIa to IIb); e.g. esters, R$^1$—CH$_2$—COOR$^3$; substituted amides, R$^1$—CH$_2$—C(O)NR$^4$R$^5$, oxazolines,

and nitriles, R$^1$CH$_2$C≡N; wherein R$^3$, R$^4$ and R$^5$ are independently selected from the groups defined by R$^1$ and aryl, and n is an integer from 1-5, may be accomplished by methods that are known to those skilled in the art.

More specifically, protection of a carboxyl group by conversion to ester, amide, oxazoline, or nitrile and subsequent regeneration of the carboxyl group is generally known and reported in several sources in the chemical literature including, R. T. Morrison and R. N. Boyd, *Organic Chemistry*, Third Edition, published by Allyn and Bacon, Inc., of Boston, Mass. in 1973, and R. B. Wagner and H. D. Zook, *Synthetic Organic Chemistry*, published by John Wiley and Sons, Inc., of New York in 1953.

The esters, R$^1$—CH$_2$—COOR$^3$ wherein R$^1$ and R$^3$ are as defined above, include any alkyl or aryl ester, particularly of propionic acid. For example, to form a suitable ester, propionic acid is esterified with t-butanol in the presence of an acid such as sulfuric acid or p-toluenesulfonic acid with heating and azeotropic removal of water using benzene.

The amides, R$^1$—CH$_2$—C(O)NR$^4$R$^5$ wherein R$^1$, R$^4$ and R$^5$ are as defined above, include any dialkyl diamide particularly of a carboxylic acid, e.g. pripionic acid. For instance, to form the amide, propionic acid is converted to propionyl chloride using thionyl chloride followed by treatment with a dialkyl amine and isolation or the amide.

The oxazolines,

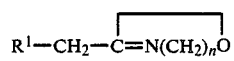

wherein R$^1$ and n are as defined above, may be purchased or prepared by treatment of the carboxylic acid or acid chloride with an amino alcohol and subsequent removal of water. After the addition of the Ar group, the carboxylic acid may be regenerated by treatment with water and mineral acid.

The nitriles, e.g., R$^1$—CH$_2$—C≡N wherein R$^1$ is as defined above, may be purchased from commercially available sources or may be prepared by forming the amide and dehydrating the amide so produced with phsophorus pentoxide or a similar dehydrating agent. After addition of the AR group, the nitrile may be reconverted to the corresponding acid by treatment with water and mineral acid. The nitrile may be any alkyl (R$^1$) substituted acetonitrile, e.g. R$^1$—CH$_2$C≡N wherein R$^1$ is as described above.

In Step H, the compound II(b) is treated with a strong base, i.e. an alkyl metal, such as n-butyl lithium, n-butyltin, n-butylzinc, or lithium N,N-diisopropylamide under conditions known in the art to produce compound II, wherein R$^1$, M and Y are as defined above.

Step B (the asymmetric coupling of compound II with ArX) and Step C (the hydrolysis to the optically active arylalkanoic acid), wherein Ar, R$^1$, X, and Y are as defined above, are performed as described above.

Steps D, J, K, B and C

In another aspect of the process of this invention, Steps D, J, K, B and C are utilized.

Step D is performed to produce a compound of formula IIb in the manner described above.

In Step K Compund IIb is treated with a strong lithium base, i.e. an alkyl or aryl lithium, such as n-butyllithium, or phenyllithium, or lithium N,N-diisopropylamide, under conditions known in the art to produce compound IId wherein R$^1$ and Y are as defined above and Li is lithium. Compound IIb thus "activated" may be treated with an alkyl metal such as n-butyltin or n-butylzinc or a metal halide such as tin(II) chloride or zinc(II) chloride, under conditions known in the art to produce Compound II, wherein R$^1$, M and Y are as defined above.

Steps B and C, wherein R$^1$, Ar, X and Y are as defined above, are preformed as is described above.

Steps D, E, G, B and C

In another aspect of the process of this invention, Steps D, F, G, B and C are used. Step D is performed to produce the compound of formula II(b) in the manner described above.

Step E describes the α-halogenation of an ester, amide, nitrile or oxazoline using a halogenating agent such as phosphorus(III) halide, phosphorus(V) halide, antimony (III) halide, antimony(V) halide and the like to produce the compound of formula II(c).

These halogenation methods are known in the art and are taught in the Morrison and Boyd and Wagner and Zook references cited above, in addition to other available references.

In Step G, compound II(c) is treated with a metal, such as lithium, tin or zinc, or a strong base such as n-butyllithium, to produce the compound of formula II. The reaction replacing a halogen with a metal is taught in Morrison and Boyd and Wagner and Zook references cited above, in addition to other available references.

Step B (the asymmetric coupling of II with ArX) and Step C [the hydrolysis to the chiral (optically active) arylalkanoic acid], wherein Ar, $R^1$, X and Y are as defined above, are also described above.

Steps F, G, B and C

In another aspect of this invention, Steps F, G, B and C are utilized.

Step F describes the direct halogenation of compound IIa, wherein $R^1$ and Y are as described above. In certain aspects, compound IIa wherein Y is carboxyl is halogenated directly to compound II(c) using halogenation agents known in the art, and also described for Step E above.

Steps G, B and C, wherein $R^1$, Ar, X and Y are as described herein, are also described above.

One skilled in this art will recognize that a judicious choice of starting materials, protecting groups, metals, aryl halides, catalysts, solvents, reaction times and temperatures are necessary to optimize the process of this invention. For instance, solvent interactions with the catalysts, starting materials and metals must be avoided.

Reaction times, temperatures and material ratios for conducting the process of this invention are generally not considered to be critical. However, it has been found convenient to conduct Step B in a temperature range of about −100° C. to about 100° C. Presently, the preferred coupling temperature is between about −80° C. and ambient temperature. Typical reaction times are between about 0.5 to about 24 hours. Suitable yields have been obtained by utilizing a range of the metal compound including an excess of the metal compound, e.g., lithium N,N-diisopropylamide, tin(II) chloride, zinc or zinc bromide, such as in the range of about 1.1 to 2.5 equivalents.

The hydrolytic removal of the protecting group in Step C to form the carboxylic acid portion of the molecule may be performed by methods that are known in the art. Various combinations of times, temperatures and material ratios may be chosen.

The process of this invention may also include the further dehalogenation of compound, Ar—CH($R^1$)—COOH, wherein Ar is, for example 5-bromo-6-methoxy-2-naphthyl, 5-chloro-6-methoxy-2-naphthyl, as described below to produce compounds wherein Ar is 6-methoxy-2-naphthyl. The process includes the pharmaceutically acceptable salts of 2-(6-methoxy-2-naphthyl)propionic acid.

More specifically the 2-(6-methoxy-2-naphthyl)propionic acid precursors are represented by the compounds of formula (IV)

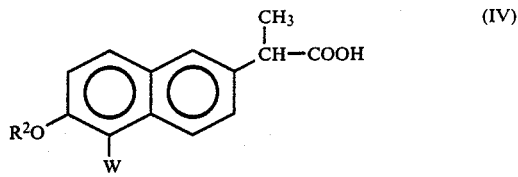

wherein $R^2$ is methyl and W is selected from chlorine and bromine. These naproxen precursors also include the salts of the compounds of formula (IV).

The compounds of formula (IV) in form of their racemic mixtures are known compounds. For example, the compound (d,1)-2-(5-bromo-6-methoxy-2-naphthyl)propionic acid is described in German Pat. No. 1,934,460 and compounds to the compound of formula (IV) wherein $R^2$ is methyl, and W is bromo. The compound for formula (IV) wherein $R^1$ is methyl and W is chloro is described as a racemic mixture in Belgian Pat. No. 752,627. The compounds of formula (IV) wherein $R^2$ is hydrogen and W is halogen are described as racemic mixtures in German Application No. 1793825 and in Italian Patent Application No. 25778A/76.

After the 2-(6-methoxy-2-naphthyl)propionic acid (naproxen) precursor of formula (IV) has been obtained in an optically pure or enhanced form it can be converted into naproxen or pharmaceutically acceptable salts thereof. For the compounds of formula (IV) wherein $R^2$ is methyl and W is halogen, the conversion to naproxen involves dehalogenation of the compounds of formula (IV). This process thus entails the replacement of haolgen with hydrogen. The 2-(5-halo-6-methoxy-2-naphthyl)propionic acid precursor of naproxen can be subjected to dehalogenation reactions which do not affect the structure of the remainder of the molecule during the formation of naproxen. A suitable method comprises the reaction of the unresolved of resolved 5-halo compounds of formula (IV) with an earth alkaline metal alcoholate such as magnesium alcoholate, for example, magnesium methylate and a tertiary amine such as tri(lower)alkyl amines, for example, triethylamine in an inert solvent such as the alcohol or alkanol from which the alcoholate or alkanolate is derived. The reaction is conducted between about 30° C. and the reflux temperature of the solvent. For example, a mixture of magnesium powder, methanol and a molar excess of triethylamine are mixed and the mixture maintained under an inert atmosphere such as a nitrogen atmosphere. Optically enhanced or resolved 2-(5-halo-6-methoxy-2-naphthyl)propionic acid is added in an anhydrous methanol solution. After the reaction is completed, i.e. after about one hour at reflux temperature, hydrochloric acid is added to the reaction mixture to dissolve all the remaining magnesium. From the reaction mixture naproxen can be recovered according to known methods. For example, the reaction mixture containing naproxen can be poured into water and extracted with a suitable solvent such as methylene chloride. The organic layer is separated, washed with water and pure naproxen crystallizes out. In another variant, the naproxen precursor of formula (IV) is reacted with at least 2, preferably 2 to 50, mole equivalents (calculated on the basis of aluminum) of a nickel aluminum or cobalt aluminum alloy in the presence of at least 2, preferably 2 to 50, mole equivalents of alkali metal hydroxide in an inert solvent until the 5-halo group is removed. The preferred nickel aluminum or cobalt aluminum alloys have a particle size of under one millimeter and the aluminum concentration should be at least 10% by weight of the alloy. Suitable alkali metal hydroxides are sodium hydroxide, potassium hydroxide or lithium hydroxide. The reaction is conducted in an inert solvent which is preferably methanol, ethanol, propanol, isopropanol, tertiary butanol, tetrahydrofuran, or dioxan. The reaction temperature is between about 0° C. and about the reflux temperature of the solvent, preferably at least 40° C. The reaction time is about 15 minutes to about 12 hours.

The unresolved or resolved 5-halo compounds of formula (IV) can be also reacted directly with a mixture of magnesium (preferably as a powder having a particle size of less than one millimeter), a lower alkanol and optionally a molar excess of an aliphatic amine until naproxen is formed. This reaction is conducted at a temperature of from about 0° C. to the reflux temperature of the reaction mixture, preferably at least 20° C. and under an inert atmosphere such as nitrogen. The time required for reduction of the 5-halo group depends upon the reaction temperatue. Usually from about 10 minutes to about 12 hours is sufficient for this reaction. At reflux temperatures, the reaction is completed within an hour.

Alternatively, the 5-halo compound of formula (IV) is treated with Raney nickel in an inert organic solvent such as a lower alkanol, an ester having up to 6 carbon atoms such as ethyl acetate, or a lower alkanoic acid such as acetic acid, propionic acid etc., optionally under hydrogen. The reaction is carried out at a temperature of at least 0° C. and preferably above 20° C. for from about 10 minutes to about 24 hours. Reflux temperature is preferred.

In a further alternative, the 5-halo compounds of formula (IV) are treated with palladium-on-charcoal, platinum or platinum oxide with hydrogen in an inert organic solvent such as those described for treatment with Raney nickel. The reaction is carried out at a temperature of from about 0° C. up to the reflux temperature of the solvent, room temperature being preferred, for from about 10 minutes to 12 hours.

N aproxen obtained from either dehalogenation of the 5-halo compound of formula (IV) can be further enhanced by resolution and/or recrystallization to obtain material of very good optical rotation, i.e. with $[\alpha]_D$ being between $+62°$–$67°$ (chloroform). The acid may be further converted to the pharmaceutically acceptable salts thereof, preferably the sodium salt.

The process of the present invention utilizes as starting materials compounds of the formula:

$$\begin{array}{c} R^1 \\ | \\ M-CH-Y' \end{array} \quad (II)$$

wherein $R^1$ is a lower alkyl radical having from 1 to 8 carbon atoms inclusive or a cycloalkyl radical having from 3 to 8 carbon atoms inclusive; M is lithium, tin, tin halide, zinc or zinc bromide; Y' is defined as a a metal salt of a carboxyl group, —C(O)OM; an alkoxycarbonyl group; —C(O)OR³; a substituted aminocarbonyl group, —C(O)NR⁴R⁵; or a nitrile group, —C≡N; an oxazolinyl group,

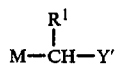

wherein M is as defined above, $R^3$, $R^4$ and $R^5$ are independently defined as $R^1$, and n is an integer from 1-5.

In this invention some novel intermediates are formed including structure II as described herein. More specifically, novel intermediates include structure II wherein $R^1$ is lower alkyl, such as methyl, M is Li and Y' is as defined herein. Particularly preferred are the structures wherein $R^1$ is methyl, Y' is —C≡N and M is lithium. Novel compounds of formula I include those wherein Ar is 6-methoxy-2-napthyl, $R^1$ is methyl, and Y' is as defined herein. More specifically, novel structure of formula I having the (S)-configuration is defined wherein Ar is 6-methoxy-2-naphthyl, $R^1$ is methyl;

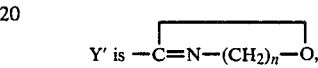

wherein n is 2.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

If desired, the compounds of formula I herein may be further enhanced into their optical antipodes having higher optical purity by fractional crystallization or by conventional resolution means; for example by separation (e.g. fractional crystallization) of the diastereomeric salts formed by the reaction of these compounds with optically active bases. Exemplary of such optically active bases are the optically active forms of cinchonidine, brucine, N-methylglucamine, α-phenethyl amine and the like. The separated pure diastereomeric salts may then be cleaved by standard means to afford the respective optical isomers of the compounds of Formula I. For instance, the optical activity 2-(6-methoxy-2-naphthyl) propionic acid and its precursors may be further enhanced, if desired, according to methods described in U.S. Pat. No. 4,246,164 and 4,246,193, and U.S. application Ser. No. 382,499, all of which are incorporated herein by reference.

The pharmaceutically acceptable non-toxic salt derivatives of the compounds of formula I are prepared by treating the free acids with an appropriate amount of pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, maganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, isopropanol, butanol, acetone, dioxane or tetrahydrofuran. The molar ratio of compounds of formula I to base used are chosen to provide the ratio desired for any particular salt. For preparing, for example, the calcuim salts or the magnesium salts the free acid starting material of formula I can be treated with at least one-half molar equivalent of pharmaceutically acceptable base to yield a neutral salt. When the aluminum salts of the compounds of formula I are prepared, at least one-third molar equivalent of the pharmaceutically acceptable base is employed if a neutral salt product is desired. Presently preferred salts of this invention include the alkali metal salts of formula I, particularly those of a compound of formula I and sodium. Presently more preferred salts are the sodium salts of formula I wherein the aryl group Ar is 6-methoxy-2-naphthyl. A presently most preferred salt is the sodium salt of 2-(6-methoxy-2-naphthyl)propinoic acid, particularly the d-isomer having the S-configuration.

The salts of the compounds of formula I can be reconverted to their respective free acids by acidifying said salts with an acid, preferably an inorganic acid, e.g., hydrochloric acid, sulfuric acid, and the like, at temperature of from about 0° C. to about 50° C., preferably at room temperature.

The pharmaceutically acceptable non-toxic esters of formula I are prepared by esterifying the corresponding free acids with an alcohol corresponding to the desired ester, i.e., an alkanol having up to 8 carbon atoms. This reaction is conducted in the presence of a strong acid, such as boron trifluoride, hydrogen chloride, sulfuric acid, p-toluenesulfonic acid, and the like. Since the alcohol reagent used in the esterification is a liquid at the reaction temperature, the alcohol can be the reaction solvent. Optionally, the reaction can be carried out in an inert organic solvent in which the free acid and the alcohol are soluble, such as a hydrocarbon solvent, e.g., hexane, isooctane, decane, cyclohexane, benzene, toluene, or xylene; a halogenated hydrocarbon solvent, e.g., methylene chloride, chloroform, or dichlorethane; or an ether solvent, e.g., diethyl ether, dibutyl ether dioxane, or tetrahydrofuran; and the like. The reaction is conducted at from about 0° C. to the reflux temperature of the reaction mixture, preferably using hydrogen chloride as a catalyst at a temperature of from about 15° C. to about 35° C.

The product, Ar—CH($R^1$)—COOH, wherein Ar and $R^1$ are as defined above is isolated by conventional means such as diluting the reaction mixture with water, extracting the resulting aqueous mixture with a water-immiscible inert organic solvent, such as diethyl ether, benzene, methylene chloride, and the like, combining the extracts, washing the extracts with water to neutrality and then evaporating under reduced pressure.

Typical non-toxic esters which can be prepared from Ar—CH($R^1$)—COOH are those ester derivatives prepared from methyl alcohol, ethyl alcohol, propyl alcohol, isopropyl alcohol, butyl alcohol, 2-butyl alcohol, 2-pentyl alcohol, isopentyl alcohol, 2-hexyl alcohol, and the like.

Alternatively, the alkyl esters of Ar—CH($R^1$)—COOH can be prepared by transesterification, according to methods known in the art. It is preferred in preparing the esters via transesterification to go from a lower ester to a higher ester, e.g., from the methyl ester, for example, to the isoamyl ester, for example. However, by using a substantial excess of a lower alcohol, a higher ester can be transesterified to a lower ester; thus, for example, by using a substantial excess of ethanol, the hexyl ester can be converted by transesterification to the ester.

In still another alternative, the esters of Ar—CH($R^1$)—COOH can be prepared by reacting the free acid with the appropriate diazoalkane, such as diazomethane, diazo-n-hexane, or diazo-i-propane in an aprotic organic solvent at low temperature.

DESCRIPTION OF PREFERRED EMBODIMENTS

A presently preferred process of this invention for the preparation of optically active compounds of formula I utilizes Steps A, B, and C as described herein, particularly wherein Ar is substituted naphthyl, $R^1$ is alkyl, Y is t-butoxycarbonyl and M is lithium.

An embodiment of this present process utilizes Steps of A, B and C as described herein wherein Ar as substituted naphthyl is 5-bromo-6-methoxy-2-naphthyl or 5-chloro-6-methoxy-2-naphthyl with subsequent removal of the halogen to produce naproxen.

A presently more preferred process utilizes steps A, B, and C as described above, wherein $R^1$ is alkyl, Ar is substituted naphthyl, Y is —COOLi, M is lithium, and the dipolar aprotic solvent is tetrahydrofuran.

A presently most preferred process utilizes steps A, B, and C as described above, wherein $R^1$ is methyl, Ar is 6-methoxy-2-naphthyl, Y is —COOLi, M is lithium, the chiral (optically active) transition metal catalyst is [(R)-1,2-bis(diphenylphosphino)-1-phenylethane]nickel(II) chloride and the dipolar aprotic solvent is tetrahydrofuran.

Presently preferred compounds prepared by this process include the optically active substituted naphthyl alkanoic acids. Especially presently preferred is the substituted naphthyl propionic acid of the formula:

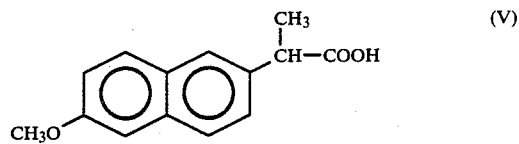

(V)

having the (S)-configuration, and the pharmaceutically acceptable salts thereof, preferably the sodium salt.

Thus, in formula I, Ar is 6-methoxy-2-naphthyl, $R^1$ is methyl, and Y is a carboxyl group.

A presently preferred ester, $R^1$—CH$_2$COOR$^3$, wherein $R^1$ and $R^3$ are as defined above, is t-butyl propionate.

Presently preferred amides, $R^1$—CH$_2$C(O)NR$^4$R$^5$ wherein $R^1$, $R^4$ and $R^5$ are as defined above as the dialkyl amides, particularly dimethyl propionamide.

A presently preferred nitrile, $R^1$—CH$_2$-C≡N, wherein $R^1$ is as described above is propionitrile.

Presently preferred oxazolines include unsubstituted and alkyl substituted oxazolines

where $R^1$ and n are as defined above, particularly 2-ethyloxazoline, wherein $R^1$ is $CH_3$ and n is 2.

Presently preferred chiral (optically active) transition metal catalysts are [(R)-1,2-bis(diphenylphosphino)-1,2-dimethylethane]-nickel(II)chloride, [(R)-1,2-bis(diphenylphosphino)-1-phenylethane]nickel(II)chloride and [(R)-1,2-bis(diphenylphosphino)-1-methylethane]-nickel(II)chloride.

Presently preferred solvents include toluene, tetrahydrofuran, dimethoxymethane, diethyl ether and mixtures thereof. A particularly preferred solvent is tetrahydrofuran.

Particular compounds falling within the scope of the present invention can be prepared by selecting an appropriate starting material, for example, from those referred to above, and then selecting particular reaction step or steps, as for example described above, to give the compound desired. In view of this disclosure, the preparation of particular compounds, including compounds falling within the scope of the present invention but not particularly described in this specification, will be apparent to those skilled in this art.

Exemplary of compounds of the present invention, as represented by formula I above, are the following illustrative compounds:
(S)-2-(4-isobutylphenyl)propionic acid;
(S)-2-(3-phenoxyphenyl)propionic acid;
(S)-2-(4-fluoro-4-biphenyl)propionic acid;
(S)-2-(2-fluoro-2-biphenyl)propionic acid; and
(S)-2-(6-methoxy-2-naphthyl)propionic acid.

Other illustrative compounds falling within the scope of the present invention include, for example:
(S)-2-(phenyl)propionic acid;
(S)-2-(4-methylphenyl)propionic acid;
(S)-2-(3-methoxyphenyl)propionic acid;
(S)-2-(2,4-dimethylphenyl)propionic acid;
(S)-2-(6-methylnaphthyl)propionic acid;
(S)-2-(6,7-dimethylnaphthyl)propionic acid;
(S)-2-(6,7-dimethoxynaphthyl)propionic acid;
(S)-2-(4-biphenyl)propionic acid;
(S)-4-(3-methyl-4-biphenyl)propionic acid;
(S)-4-(3-methoxy-4-biphenyl)propionic acid;
(S)-4-(3-methyl-4-biphenyl)propionic acid; and
(S)-4-(3-methoxy-4-biphenyl)propionic acid
which have varying degrees of anti-inflammatory activity. The above compounds having the corresponding (R)- configuration may be prepared using the appropriate chiral (optically active) catalyst.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

EXAMPLE 1

Preparation of Compounds of Formula I via Ester

To a dry 100 ml three-necked flask fitted with a magnetic stirring bar, a nitrogen inlet and a pressure equalizing dropping funnel is added 1.21 g of N,N-diisopropylamine and 20 ml of tetrahydrofuran (THF). The flask is cooled to 0° C. and 6.56 ml (10.5 mmole, 1.6M solution) of n-butyllithium is introduced via syringe. The resulting solution is stirred for 10 minutes and then cooled to −78° C. A solution of 1.36 g of t-butyl propionate in 10 ml of THF is added dropwise to the flask over a five-minute period. The resulting solution is stirred at −78° C. for one hour.

To a second 100 ml three-necked flask fitted with a magnetic stirring bar, a nitrogen inlet tube and a pressure equalizing dropping funnel is added 2.18 g of [(R)-1,2-bis(diphenylphosphino)-1-phenylethane]nickel(II) chloride and 25 ml of THF. The mixture is cooled to −78° C. and 1.25 ml (2 mmole, 1.6M solution) of n-butyllithium is added. The resulting solution is stirred at −78° C. for five minutes and then 1.9 g of 2-bromo-6-methoxynaphthalene in 10 ml of THF is added. The resulting solution is stirred for 15 minutes. The tetrahydrofuran solution of lithio t-butyl propionate is then transferred to the 100 ml flask using a double tipped needle. The resulting solution is stirred at −78° C. for 2.5 hours and then allowed to warm to ambient temperature. After allowing the solution to stir an additional 14 hours, the reaction is quenched by pouring it into 150 ml of 5% aqueous HCl. The aqueous layer is extracted three times with 75 ml of dichloromethane, and the solvent is removed using a rotary evaporator. The remaining residue is dissolved in 150 ml of methanol and 75 ml of 0.1N potassium hydroxide. The solution is refluxed for 24 hours and the methanol removed using a rotary evaporator. The remaining aqueous solution is acidified and extracted three times with 75 ml of dichloromethane. The extracts are dried over anhydrous sodium sulfate, and the solvent is removed in vacuum to give 0.33 g (18% yield) of 2-(6-methoxy-2-naphthyl)-propionic acid having the (S)-configuration.

Repeating the above procedure in a similar manner and substituting a stoichiometrically equivalent amount of:
2-naphthylbromide;
2-iodo-6-methoxynaphthalene;
2-chloro-6-methoxynaphthalene;
phenyl bromide;
4-isobutylphenyl bromide;
3-phenoxyphenyl bromide;
4-bromobiphenyl;
4-(4'-fluorophenyl)phenyl bromide; and
4-(2-fluorophenyl)phenyl bromide
for the 2-bromo-6-methoxynaphthalene there are obtained respectively the following compounds:
2-(2-naphthyl)propionic acid;
2-(6-methoxy-2-naphthyl)propionic acid;
2-(6-methoxy-2-naphthyl)propionic acid;
2-(phenyl)propionic acid;
2-(4-isobutylphenyl)bromide;
2-(3-phenoxyphenyl)propionic acid;
2-(4-biphenyl)propionic acid;
2-(4'-fluoro-4-biphenyl)propionic acid; and
2-(2-fluoro-4-biphenyl)propionic acid all having the (S)-configuration.

Repeating the above procedure in a similar manner and substituting a stoichiometrically equivalent amount of:
isopropyl propionate;
N,N-dimethylpropionamide;
2-ethylimidazoline; and
propionitrile
for the t-butyl propionate there is obtained, upon hydrolysis, in each case, 2-(6-methoxy-2-naphthyl)propionic acid having the (S)-configuration.

EXAMPLE 2

Preparation of 2-(6-Methoxy-2-naphthyl) propionic Acid Using Optically Active Catalyst Example 2 is performed in a manner similar to Example 1, with the replacement of 2.18 g of [(R)-1,2-bis(diphenylphosphino)-1-phenylethane]nickel(II) chloride with 3.0 g of [(R)-1,2-bis(diphenylphosphino)-1-phenylethane]nickel(II) bromide. About a 50% yield of 2-(6-methoxy-2-naphthyl)propionic acid is obtained having the (S)-configuration.

EXAMPLE 3

Preparation of (S)-2-(6-Methoxy-2-naphthyl)propionic Acid Using a Dilithiopropionate To a dry 100 ml three-necked flask fitted with a magnetic stirring bar, reflux condenser, a nitrogen inlet tube and a pressure equalizing dropping funnel is added 1.40 g of N,N-diisopropylamine and 30 ml of anhydrous tetrahydrofuran. The flask is cooled to 0° C. and 9.13 ml (12.6 mmole, 1.38M solution) of n-butyllithium is introduced by syringe. The resulting solution is stirred for 15 minutes and then 0.469 g of propionic acid in 10 ml of tetrahydrofuran is added to the flask over a five minute period. The solution is allowed to warm to ambient temperature and then heated to 45° C. for 1.5 hours to produce the dilithium dianion of propionic acid.

To a second 100 ml three-necked flask fitted with a magnetic stirring bar, reflux condenser, a nitrogen inlet tube and a pressure equalizing dropping funnel is added 0.24 g of [(R)-1,2-bis(diphenylphosphino)-1-phenylethane]nickel(II) chloride and 20 ml of anhydrous tetrahydrofuran. The flask is cooled to −78° C. and 0.59 ml (0.82 mmole, 1.38M solution) of n-butyllithium added. The solution is stirred for 15 minutes and then 1.42 g of 2-bromo-6-methoxynaphthalene in 10 ml of tetrahydrofuran is added. The resulting solution is stirred for 15 minutes.

The dilithium dianion of propionic acid is then transferred from the 50 ml flask to the addition funnel fitted to the second flask. The dianion is added dropwise to the reaction mixture at −78° C. over a 30 min period. The reaction mixture is allowed to warm to ambient temperature, stirred for 16 hours and poured into 175 ml of 10% hydrochloric acid. The aqueous layer is extracted three times with 75 ml of dichloromethane. The extracts were dried over anhydrous sodium sulfate and the solvent removed using a rotary evaporator to give 1.79 g of a solid material. Analysis of the solid material by gas liquid phase chromatography indicated the material to contain 38% of the desired product, (S)-2-(6-methoxy-2-naphthyl)propionic acid (MNPA, naproxen) (in a 45% chemical yield).

Repeating the above procedure in a similar manner and substituting a stoichiometrically equivalent amount of:
2-naphthyl bromide;
2-iodo-6-methoxynaphthalene;
2-chloro-6-methoxynaphthalene;
phenyl bromide;
4-iso-butylphenyl bromide;
3-phenoxyphenylbromide;
4-bromobiphenyl;
4-(4'-fluorophenyl)phenyl bromide; and
4-(2-fluorophenyl)phenyl bromide
for the 2-bromo-6-methoxynaphthalene there are obtained, respectively, the following compounds:
2-(2-naphthyl)propionic acid;
2-(6-methoxy-2-naphthyl)propionic acid;
2-(6-methoxy-2-naphthyl)propionic acid;
2-phenylpropionic acid;
2-(4-isobutylphenyl)propionic acid;
2-(3-phenoxyphenyl)propionic acid;
2-(4'-biphenyl)propionic acid;
2-(4'-fluoro-4-biphenyl)propionic acid; and
2-(2-fluoro-4-biphenyl)propionic acid each having the (S)-configuration.

EXAMPLES 4–12

Preparation of 2-(6-methoxy-2-naphthyl) Propionic Acid Using a Dilithiopropionate Examples 4–12 are performed in a manner similar to that described in Example 3. The results are shown below in Table 3. In all examples, the R- or S- configurational isomer is present in more than 70% enantiomeric excess as determined by nuclear magnetic resonance spectral analysis using an optically acive shift reagent; isolation of the acid and determining the rotation using a polarimeter; or formation of a derivative and analysis using high pressure liquid chromatography (HPLC). These techniques are described in detail by Kenoshita et al., in the *Journal of Chromatography*, vol. 202, pp. 375–9, published in 1980, and vol. 210, pp 77–81 published in 1981.

TABLE 3

Coupling of Dilithiopropioinate with 6-Methoxy-2-bromonaphthalene

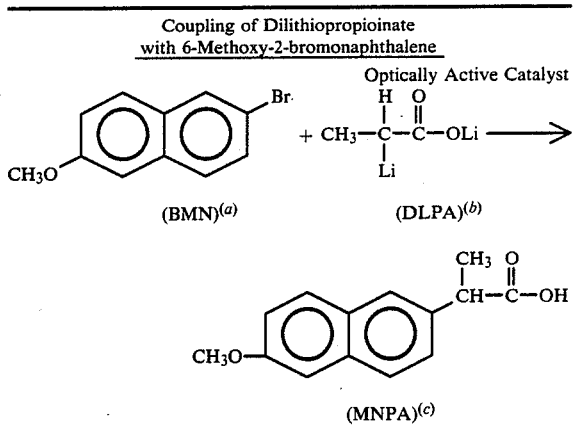

| Example | Solvent | BMN (gms) | DLPA (gms) | Catalyst** (gms) | Yield of MNPA % |
|---|---|---|---|---|---|
| 4 | THF[d] | 1.5 | .52 | CHIRAPHOS (1.3) +0.2 eq. n-butyllithium | 35 |
| 5 | THF | 1.4 | .51 | CHIRAPHOS[e] (0.25) | 45 |
| 6 | Diethyl Ether/THF (50/50) | 1.4 | .61 | PHENPHOS[e] (0.25) | 36 |
| 7 | Dimethoxyethane | 1.4 | .52 | PHENPHOS[e] (0.22) | 30 |
| 8 | THF | 1.4 | .51 | PHENPHOS[e] (0.25) | 33 |
| 9 | THF | 2.4 | .83 | PHENPHOS[f] (0.40) | 31 |
| 10 | THF | 2.3 | .80 | PROPHOS[f] (0.45) | 34 |
| 11 | THF | 1.4 | .52 | PROPHOS[f] (0.23) | 28 |
| 12 | THF | 1.4 | .51 | PROPHOS[e] | 28 |

TABLE 3-continued

Coupling of Dilithiopropioinate
with 6-Methoxy-2-bromonaphthalene

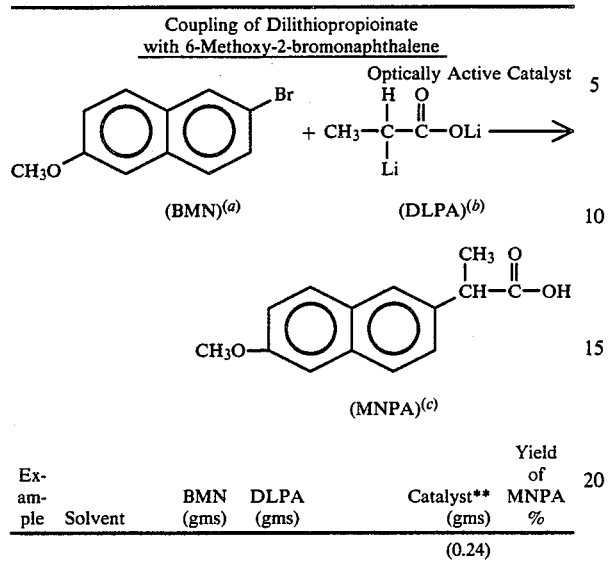

| Example | Solvent | BMN (gms) | DLPA (gms) | Catalyst** (gms) | Yield of MNPA % |
|---|---|---|---|---|---|
| | | | | (0.24) | |

**CHIRAPHOS, PHENPHOS and PROPHOS are present as the nickel(II) chloride compound.
(a)BMN is 2-bromo-6-methoxy-naphthalene.
(b)DLPA is the dilithium salt of propionic acid.
(c)MNPA is 2-(6-methoxy-2-naphthyl)propionic acid.
(d)THF is tetrahydrofuran.
(e)Where 2 equivalents of the reducing agent ethyl magnesium chloride based upon the catalyst concentration are added immediately after the addition of the organophosphorus nickel(II) chloride catalyst and tetrahydrofuran described in paragraph 2 of Example 3.
(f)Where 2 equivalents of the reducing agent n-butyllithium based upon the catalyst concentration are added immediately after the addition of the organo phosphorus nickel(II) chloride catalyst and tetrahydrofuran described in paragraph 2 of Example 3.

EXAMPLE 13

Preparation of (S)-2-(6-methoxy-2-naphthyl) propionic Acid using a Tin Reagent

To a dry 100 ml three-necked flask fitted with a magnetic stirring bar, a nitrogen inlet and a pressure equalizing dropping funnel is added 1.46 g of anhydrous tin(II) chloride and 20 ml of anhydrous tetrahydrofuran (THF). Lithium aluminum hydride (0.25 g, 6.5 mmole) is then slowly added portionwise to the tin(II) chloride. The resulting slurry is stirred for 5 minutes, and then 1.81 g of ethyl 2-bromopropionate in 5 ml THF is added dropwise followed by 1.89 g of 2-bromo-6-methoxynaphthalene in 10 ml of THF. [(R)-1-(diphenylphosphino)-2-(dimethylamino)-t-butylethane]nickel(II) chloride (0.37 g) is then added to the flask and the reaction stirred at room temperature for 24 hours. The reaction is quenched by pouring it into 150 ml of 5% aqueous HCl. The aqueous layer is extracted three times with 75 ml of dichloromethane, and the solvent removed in vacuum. The remaining residue is dissolved in 150 ml of methanol and 75 ml of 0.1N potassium hydroxide. The solution is refluxed for 24 hours, and the methanol removed using a rotary evaporator. The remaining aqueous solution is acidified and extracted three times with 75 ml of dichloromethane. The extracts are dried over sodium sulfate and the solvent removed using a rotary evaporator. Thin layer chromatographic analysis shows the presence of the desired product, 2-(6-methoxy-2-naphthyl)propionic acid, which by nuclear magnetic resonance spectral analysis in the presence of an optically active shift reagent has the (S)-configuration.

EXAMPLES 14-19

Preparation of 2-(5-Halo-6-methoxy-2-naphthyl)-propionic Acid Using a Dilithiopropionate Examples 14-19 are performed in a manner similar to that described in Example 3. The results are shown below in Table 4.

TABLE 4

Coupling of Dilithiopropionate
with 5-Halo-6-methoxy-2-bromonaphthalene

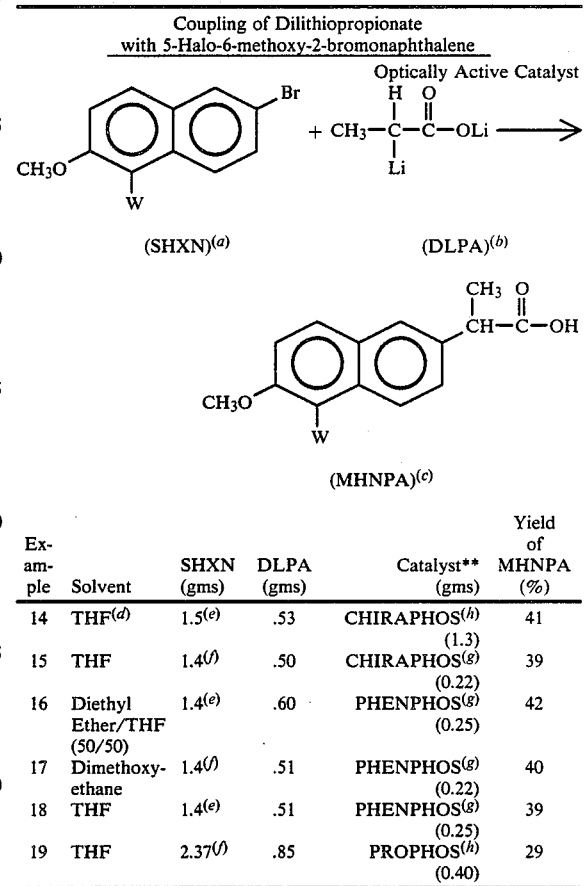

| Example | Solvent | SHXN (gms) | DLPA (gms) | Catalyst** (gms) | Yield of MHNPA (%) |
|---|---|---|---|---|---|
| 14 | THF(d) | 1.5(e) | .53 | CHIRAPHOS(h) (1.3) | 41 |
| 15 | THF | 1.4(f) | .50 | CHIRAPHOS(g) (0.22) | 39 |
| 16 | Diethyl Ether/THF (50/50) | 1.4(e) | .60 | PHENPHOS(g) (0.25) | 42 |
| 17 | Dimethoxyethane | 1.4(f) | .51 | PHENPHOS(g) (0.22) | 40 |
| 18 | THF | 1.4(e) | .51 | PHENPHOS(g) (0.25) | 39 |
| 19 | THF | 2.37(f) | .85 | PROPHOS(h) (0.40) | 29 |

**CHIRAPHOS, PHENPHOS and PROPHOS are present as the nickel(II) chloride compound.
(a)SHXN is 5-substituted-6-methoxy-2-bromonaphthalene.
(b)DLPA is the dilithium salt of propionic acid.
(c)MHNPA is 2-(5-halo-6-methoxy-2-naphthyl)propionic acid.
(d)THF is tetrahydrofuran.
(e)W is bromo.
(f)W is chloro.
(g)where 2 equivalents of the reducing agent ethyl magnesium chloride based upon the catalyst concentration are added immediately after the addition of the chloride catalyst and tetrahydrofuran described in paragraph 2 of Example 3.
(h)where 2 equivalents of the reducing agent n-butyllithium based upon the catalyst concentration are added immediately after the addition of the chloride catalyst and tetrahydrofuran described in paragraph 2 of Example 3.

Except for Examples 14 and 15 above where CHIRAPHOS produces MHNPA having the (R)-configuration, the product MHNPA is produced having the (S)-enantiomer in excess. If the S-isomer of CHIRAPHOS is used in Examples 14 and 15, (S)-MHNPA will be produced.

EXAMPLE 20

(S)-2-(6-Methoxy-2-naphthyl)-propionic acid (from the bromo precursor using Ni-Al)

A solution of 1 g of (S)-2-(5-chloro-6-methoxy-2-naphthyl)-propionic acid in 20 ml of 10% aqueous sodium hydroxide solution at 90° C. is treated with 3 g of a nickel-aluminum alloy in small portions. After stirring the mixture for two hours, it is filtered, diluted with excess dilute hydrochloric acid and extracted with methylene chloride. The organic phase is evaporated to dryness and the residue recrystallized from methylene chloride/hexane to yield (S)-2-(6-methoxy-2-naphthyl)-propionic acid after recrystallization.

EXAMPLE 21

(S)-6-(methoxy-2-naphthyl)propionic acid (from the bromo precursor using Mg)

To a 250 ml flask equipped with a reflux condenser and a nitrogen bubbler, magnesium powder (60 g) are added, further anhydrous methanol (50 ml) and triethylamine (10 g). The flask is swept with nitrogen, and the nitrogen atmosphere is maintained throughout the reaction.

The (S)-5-bromo-6-methoxy-2-naphthyl)propionic acid (0.1 mole) in methanol (15 g) is slowly added, and the mixture is heated under reflux for one additional hour after the addition of the 5-bromo-naproxen precursor is complete. The cooled mixture is mixed with 6N hydrochloric acid until no magnesium remains. The mixture is poured into water and extracted with methylene chloride. The organic layer is separated, washed with water and crystallized by concentrating the solution and adding hexane. After recrystallization, (S)-2-(6-methoxy-2-naphthyl)propionic acid is obtained.

EXAMPLE 22

2-(6-Methoxy-2-naphthyl)propionic Acid (from chloro precursor using Raney Nickel)

A solution of one g of the 5-chloro-naproxen precursor in 10 ml of anhydrous methanol is mixed with one g of Raney nickel and heated at reflux temperature for 12 hours. The mixture is filtered, and the filtrate is diluted with water. The precipitate is dried and recrystallized from acetone/hexane to yield (S)-2-(6-methoxy-2-naphthyl)propionic acid.

EXAMPLE 23

To a dry 50 ml three-necked round-bottom flask fitted with a magnetic stirrer, reflux condenser, an argon inlet tube and a pressure equalizing dropping funnel is added 1.40 g of diisopropylamine and 35 ml of anhydrous tetrahydrofuran (THF). The flask was cooled to 0° C. and 12.6 mmole of n-butyllithium is introduced via syringe. The resulting solution is stirred for ten minutes, and a solution of 0.47 g of propionic acid in 5 ml of tetrahydrofuran is added to the flask over a five-minute period. The solution is allowed to warm to ambient temperature and then heated to 45° C. for 1.5 hours.

To a second 100 ml three-neck flask fitted with a magnetic stirring bar, reflux condenser, an argon inlet tube and a pressure equalizing dropping funnel is added 0.25 g of [(R)-1,2-bis(diphenylphosphino)-1-phenylethane]nickel(II) chloride (PHENPHOS nickel(II) chloride) and 20 ml of anhydrous tetrahydrofuran. The flask is cooled to −78° C. and 0.84 mmol of n-butyllithium added. The solution is stirred for 15 minutes and then 1.42 g of 2-bromo-6-methoxynaphthalene in 10 ml of tetrahydrofuran is added dropwise. The resulting solution is stirred for 15 minutes.

The dianion of propionic acid is transferred from the 50 ml flask to the addition funnel fitted to the second flask. The dianion is added dropwise to the solution over a 30-minute period. The reaction mixture was allowed to warm to ambient temperature, stirred for 14 hours and poured into 250 ml of 10% hydrochloric acid. The aqueous layer was extracted three times with 75 ml with 0.1N potassium hydroxide. The basic extracts are acidified and extracted three times with 75 ml of dichloromethane. The extracts are dried over anhydrous sodium sulfate and concentrated to give 0.75 g of crude naproxen. Recrystallization of the crude material produces 0.42 g (30.4% yield) of naproxen having $[\alpha]_D^{25} = +54.4°$, indicating a 90:10 ratio of the (S)-enantiomer to the (R)-enantiomer.

The methyl ester of the arylpropionic acid is prepared by refluxing the acid in methanol containing a catalytic amount of sulfuric acid.

Proton nuclear magnetic resonance spectral examination of the splitting of the methyl ester singlet in the presence of the chiral shift reagent, tris[3-heptafluoropropyl)hydroxymethylene-d-camphorato]europium (III), confirms the enantiomeric ratio to be 90:10 of the S- to R-configuration.

EXAMPLE 24

Substitution of an equivalent quantity of [(R)-1,2-bis(-diphenylphosphino)-1,2-dimethylethane]nickel(II) chloride (CHIRAPHOS nickel(II) chloride) in the procedure of Example 30 for PHENPHOS nickel(II) chloride affords (R)-2-(6-methoxy-2-naphthyl)propionic acid. Use of S-CHIRAPHOS will afford the (S)-acid.

EXAMPLE 25

Substitution of an equivalent quantity of [(R)-1,2-bis(-diphenylphosphino)-1-methylethane]nickel(II) chloride (PROPHOS nickel(II) chloride) in the procedure of Example 30 for PHENPHOS nickel(II) chloride affords (S)-2-(6-methoxy-2-naphthyl)propionic acid.

EXAMPLE 26

This example illustrates the conversion of free carboxylic acid of Example 1–25 to various salts.

To a solution of 300 mg of (S)-2-(6-methoxy-2-naphthyl)-propionic acid in 5 ml of methanol is added a 1 molar equivalent of sodium hydroxide, in the form of a 0.1N solution. The solvent is evaporated in vacuo and the residue is taken up in 2 ml of methanol, followed by precipitation with ether, to yield crude sodium (S)-2-(6-methoxy-2-naphthyl)propionate.

Likewise, other salts, e.g., ammonium and potassium (S)-2-(6-methoxy-2-naphthyl)propionate, are prepared by substituting ammonium hydroxide and potassium hydroxide for sodium hydroxide.

EXAMPLE 27

Direct Interconversion of Acid Addition Salts of Acids of Formula I

This example illustrates the interconversion of carboxylic acid salts of the compound of formula I to various salts.

To a solution of 50 ml of 50% aqueous sulfuric acid is added 1.0 g of (S)-2-(6-methoxy-2-naphthyl)propionyl acetate after dissolving, the solution is evaporated to an oil. The product is suspended in ethanol and filtered, air dried and recrystallized from methanol/acetone to yield (S)-2-(6-methoxy-2-naphthyl)propionyl sulfate.

EXAMPLE 28

This example illustrates conversion of the free carboxylic acids of Examples 1–26 to various other esters.

A solution of 300 mg of (S)-2-(6-methoxy-2-naphthyl)propionic acid in 5 ml of isobutyl alcohol is saturated with hydrogen chloride. After 24 hours, the excess alcohol is distilled off in vacuo and the residue is purified by chromatography using an alumina substrate to yield isobutyl (S)-2-(6-methoxy-2-naphthyl)propionate.

Likewise, other esters, e.g., pentyl, isoamyl, hexyl octyl, nonyl, decyl, dodecyl and the like are obtained by substituting the isobutyl alcohols with the corresponding alcohol, e.g., pentyl, isoamyl, hexyl, octyl, nonyl, decyl, dodecyl alcohol and the like.

While the present invention has been described with reference to the specific embodiments thereof, it should be understood by those skilled in this art that various changes may be made and equivalents may be substituted without departing from the true spirit and scope of the invention. In addition, many modifications may be made to adopt a particular situation, material, or composition of matter, process, process step or steps, or the present objective to the spirit of this invention without departing from its essential teachings.

What is claimed is:

1. A process for preparing an optically active compound of the formula:

wherein:
Ar is a substituted naphthyl moiety selected from the group consisting of 6-methoxy-2-naphthyl and 5-Z-6-methoxy-2-naphthyl, wherein Z is chlorine or bromine; and
Y is a carboxyl group, a metal salt of a carboxyl group, an alkoxycarbonyl group, a substituted aminocarbonyl group, a nitrile group or a oxazolinyl group;
which comprises:
contacting a compound of the formula:

wherein Y is as defined above with a naphthyl halide of the formula:

wherein:
Ar is as defined above and
X is halogen,
in the presence of a chiral transition metal catalyst of the formula (LL*)QZT wherein Q is a transition metal selected from the group consisting of palladium and nickel; Z and T are independently halogen; and LL* is a chiral tertiary diphosphine compound capable of acting as a bidentate ligand with Q to form a 5-membered ring, and optionally in the presence of a dipolar, aprotic solvent, to form the compound of formula VI.

2. A process for preparing a single stereoisomer of a compound of the formula:

wherein:
Ar is a substituted naphthyl moiety selected from the group consisting of 6-methoxy-2-naphthyl and 5-Z-6-methoxy-2-naphthyl, wherein Z is chlorine or bromine; and
Y is a carboxyl group, a metal salt of a carboxyl group, an alkoxycarbonyl group, a substituted aminocarbonyl group, a nitrile group or a oxazolinyl group;
which comprises:
contacting a compound of the formula:

wherein Y is as defined above with a naphthyl halide of the formula:

wherein:
Ar is as defined above and
X is halogen,
in the presence of a chiral transition metal catalyst of the formula (LL*)QZT wherein Q is a transition metal selected from the group consisting of palladium and nickel; Z and T are independently halogen; and LL* is a chiral tertiary diphosphine compound capable of acting as a bidentate ligand with Q to form a 5-membered ring, and optionally in the presence of a dipolar, aprotic solvent, to form the compound of formula VI.

3. A process for preparing a material consisting essentially of a single stereoisomer of a compound of the formula:

wherein:
Ar is a substituted naphthyl moiety selected from the group consisting of 6-methoxy-2-naphthyl and 5-Z-6-methoxy-2-naphthyl, wherein Z is chlorine or bromine; and
Y is a carboxyl group, a metal salt of a carboxyl group, an alkoxycarbonyl group, a substituted aminocarbonyl group, a nitrile group or a oxazolinyl group;
which comprises:
contacting a compound of the formula:

wherein Y is as defined above with a naphthyl halide of the formula:

wherein:
Ar is as defined above and
X is halogen,
in the presence of a chiral transition metal catalyst of the formula (LL*)QZT wherein Q is a transition metal selected from the group consisting of palladium and nickel; Z and T are independently halogen; and LL* is a chiral tertiary diphosphine compound capable of acting as a bidentate ligand with Q to form a 5-membered ring, and optionally in the presence of a dipolar, aprotic solvent, to form the compound of formula VI.

4. The process of any one of claims 1, 2, or 3 wherein Ar is 6-methoxy-2-naphthyl.

5. The process of any one of claims 1, 2, or 3 wherein Y is a carboxyl group, an alkoxycarbonyl group, or a metal salt of a carboxyl group.

6. The process of any one of claims 1, 2, or 3, which further comprises:
 (a) hydrolyzing any ester, amide, oxazoline, nitrile, or metal salt of a carboxyl group formed to the corresponding α-naphthylpropionic acid; optionally followed by:
 (b) converting the acid into a pharmaceutically acceptable ester thereof by treating with a pharmaceutically acceptable alkanol; or
 (c) converting the acid into a pharmaceutically acceptable salt thereof by treating with a pharmaceutically acceptable base.

7. The process of any one of claims 1, 2, or 3 wherein Ar is 5-Z-6-methoxy-2-naphthyl, which further comprises dehalogenation of the 5-Z group.

8. The process of any one of claims 1, 2, or 3 wherein LL* is selected from the group consisting of alkyl- and aryl-substituted 1,2-bis(diphenylphosphino)ethanes.

9. The process of claim 8 wherein the catalyst is selected from the group consisting of

[(R)-1,2-bis(diphenylphosphino)-1,2-dimethylethane]-nickel(II) chloride,
[(R)-1,2-bis(diphenylphosphino)-1-phenylethane]nickel(II) chloride, and
[(R)-1,2-bis(diphenylphosphino)-1-methylethane]nickel(II) chloride.

10. A process for preparing (S)-6-methoxy-2-naphthylpropionic acid, or a pharmaceutically acceptable salt or ester thereof which comprises
 (a) contacting 6-methoxy-2-bromonaphthalene with dilithiopropionate in the presence of a catalyst comprising the reaction product of n-butyllithium and a compound selected from the group consisting of:
 [(R)-1,2-bis(diphenylphosphino)-1,2-dimethylethane]-nickel(II) chloride,
 [(R)-1,2-bis(diphenylphosphino)-1-phenylethane]nickel(II) chloride, and
 [(R)-1,2-bis(diphenylphosphino)-1-methylethane]nickel(II) chloride
 in the presence of a dipolar, aprotic solvent;
 (b) hydrolyzing the resulting lithium propionate salt to afford (S)-6-methoxy-2-naphthylpropionic acid; and, optionally,
 (c) converting the acid into a pharmaceutically acceptable ester thereof by treating with a pharmaceutically acceptable alkanol; or
 (d) converting the acid into a pharmaceutically acceptable salt thereof by treating with a pharmaceutically acceptable base.

* * * * *